United States Patent
Actis Goretta et al.

(10) Patent No.: US 10,709,159 B2
(45) Date of Patent: Jul. 14, 2020

(54) INCREASING THE BIOAVAILABILITY OF FLAVAN-3-OLS WITH CARBOHYDRATES WITH A LOW GLYCEMIC INDEX

(71) Applicant: NESTEC S.A., Vevey (CH)

(72) Inventors: Lucas Actis Goretta, Lausanne (CH); Marcia Da Silva Pinto, Lausanne (CH); Maria Belen Sanchez Bridge, Penthaz (CH); Emmanuelle Bertschy, Vich (CH); Antoine Leveques, Epalinges (CH)

(73) Assignee: Societe des Produits Nestle S.A., Vevey (CH)

( * ) Notice: Subject to any disclaimer, the term of this patent is extended or adjusted under 35 U.S.C. 154(b) by 0 days.

(21) Appl. No.: 14/646,127

(22) PCT Filed: Nov. 29, 2013

(86) PCT No.: PCT/EP2013/075102
§ 371 (c)(1),
(2) Date: May 20, 2015

(87) PCT Pub. No.: WO2014/083161
PCT Pub. Date: Jun. 5, 2014

(65) Prior Publication Data
US 2015/0289552 A1    Oct. 15, 2015

(30) Foreign Application Priority Data
Nov. 29, 2012  (EP) ..................................... 12194896

(51) Int. Cl.
| | | |
|---|---|---|
| *A61K 31/353* | (2006.01) |
| *A61Q 19/00* | (2006.01) |
| *A23L 33/125* | (2016.01) |
| *A23L 5/00* | (2016.01) |
| *A23L 2/52* | (2006.01) |
| *A61K 8/97* | (2017.01) |
| *A61K 8/60* | (2006.01) |
| *A61K 8/49* | (2006.01) |
| *A23L 2/60* | (2006.01) |
| *A23K 20/163* | (2016.01) |
| *A23L 29/30* | (2016.01) |
| *A23L 33/105* | (2016.01) |
| *A23L 33/10* | (2016.01) |
| *A23K 20/111* | (2016.01) |
| *A23L 7/00* | (2016.01) |

(52) U.S. Cl.
CPC ........... *A23L 33/125* (2016.08); *A23K 20/111* (2016.05); *A23K 20/163* (2016.05); *A23L 2/52* (2013.01); *A23L 2/60* (2013.01); *A23L 5/00* (2016.08); *A23L 29/30* (2016.08); *A23L 33/10* (2016.08); *A23L 33/105* (2016.08); *A23L 33/105* (2016.08); *A61K 8/498* (2013.01); *A61K 8/60* (2013.01); *A61K 8/97* (2013.01); *A61K 31/353* (2013.01); *A61Q 19/00* (2013.01); *A23L 7/00* (2016.08); *A23V 2002/00* (2013.01); *A61K 2800/10* (2013.01); *A61K 2800/92* (2013.01)

(58) Field of Classification Search
CPC ........ A23L 33/15; A23L 33/105; A23L 33/16; A61K 31/355
See application file for complete search history.

(56) References Cited

U.S. PATENT DOCUMENTS

| | | | |
|---|---|---|---|
| 2006/0159724 A1 | 7/2006 | Bell | |
| 2013/0280357 A1* | 10/2013 | Coy | ......................... A23G 1/40 424/776 |

FOREIGN PATENT DOCUMENTS

| | | |
|---|---|---|
| FR | 2899768 | 10/2007 |
| JP | 2002291441 A | 10/2002 |
| JP | 2005046005 | 2/2005 |
| JP | 2008142074 | 6/2008 |
| WO | 0211562 | 2/2002 |
| WO | 2004110175 | 12/2004 |
| WO | 2005004630 | 1/2005 |
| WO | 2012092916 | 7/2012 |

OTHER PUBLICATIONS

Shanmugavelan et al. Carbohydrate Research 380 (2013) 112-117 (Year: 2013).*
Shim et al. "Digestive stability and absorption of green tea polyphenols: Influence of acid arid xylitol addition" Food Research International, 2012, vol. 45, pp. 204-210.

* cited by examiner

Primary Examiner — Samantha L Shterengarts
(74) Attorney, Agent, or Firm — K&L Gates LLP

(57) ABSTRACT

The present invention relates generally to the field of flavan-3-ols. In particular, the present invention provides a way to increase the bioavailability of flavan-3-ols. Embodiments of the present invention relate to the use of at least one carbohydrate with a glycemic index of less than 50 in a composition comprising at least one flavan-3-ol for increasing the bioavailability of said flavan-3-ol.

17 Claims, 2 Drawing Sheets

INCREASING THE BIOAVAILABILITY OF FLAVAN-3-OLS WITH CARBOHYDRATES WITH A LOW GLYCEMIC INDEX

CROSS REFERENCE TO RELATED APPLICATIONS

The present application is a National Stage of International Application No. PCT/EP2013/075102, filed on Nov. 29, 2013, which claims priority to European Patent Application No. 12194896.2, filed on Nov. 29, 2012, the entire contents of which are being incorporated herein by reference.

The present invention relates generally to the field of flavan-3-ols. In particular, the present invention provides a way to increase the bioavailability of flavan-3-ols. Embodiments of the present invention relate to the use of at least one carbohydrate with a glycemic index of less than 50 in a composition comprising at least one flavan-3-ol for increasing the bioavailability of said flavan-3-ol.

Flavan-3-ols (including for example "catechins") are present in several food sources such as cocoa, tea and apples. Several epidemiological, in vitro and in vivo studies have associated the presence of these compounds to health promoting effects such as antioxidative and anti-inflammatory benefits (Aron, P. M., et al., 2008, Molecular Nutrition & Food Research 52, 79-104).

In general flavan-3-ols are subjected to several phase II enzymes leading to conjugation with methyl groups (catechol-O-methyltransferases—COMT), sulfate groups (sulphotransferases—SULT) and glucuronyl groups (uridine-5'-diphosphate glucuronosyl-transferases—UDPGT). However, EGCG, the main flavan-3-ol present in green tea, has been reported to be present in human plasma mainly in its native form (Williamson et al., 2011, Mol Nutr Food Res 55, 864-873).

The oral bioavailability of, e.g., the green tea flavan-3-ols is low, resulting in systemic flavan-3-ols levels in humans which are many fold lower than the effective concentrations determined in in vitro systems (Lambert et al., 2007, Mol. Pharmaceutics 4, 819-825). Many approaches to increase bioavailability of flavan-3-ols from green tea have been reported in literature such as the administration of tea in combination with piperine, an alkaloid present in black pepper, and peracetylation of EGCG. Another strategy to improve the absorption of flavan-3-ols is the administration during a fasting state, however, it is important to notice that some human studies have shown that high doses of green tea preparations can be potentially toxic (Chow et al., 2005, Clinical Cancer Research 11, 4627-4633; Bonkovsky, 2006, Ann Intern Med 144, 68-71).

Hence there is a need in the art for alternative ways to improve the absorption of flavan-3-ols while avoiding overdosing of flavan-3-ols.

Any reference to prior art documents in this specification is not to be considered an admission that such prior art is widely known or forms part of the common general knowledge in the field.

The object of the present invention was it therefore to improve the state of the art and in particular to provide a way to administer flavan-3-ols while ensuring effective absorption and a high bioavailability, or to at least to provide a useful alternative to what is known in the art.

The inventors were surprised to see that the object of the present invention could be achieved by the subject matter of the independent claims. The dependent claims further develop the idea of the present invention.

Accordingly, the present invention provides a new approach for increasing the absorption of the flavan-3-ols. In accordance with the present invention this is achieved by co-administration of these compounds with carbohydrates with a glycemic index of less than 50.

As used in this specification, the words "comprises", "comprising", and similar words, are not to be interpreted in an exclusive or exhaustive sense. In other words, they are intended to mean "including, but not limited to".

The present inventors have conducted extensive in vitro experiments using a Caco-2 cell model and could show that the co-administration of flavan-3-ols with certain carbohydrates can increase the absorption of flavan-3-ols.

It was found that this works particularly well with carbohydrates with a glycemic index of less than 50.

The glycemic index (GI) is a measure of how quickly the level of glucose rises in blood after the consumption of a particular type of food relative to consumption of pure glucose. Glucose has a glycemic index of 100.

The determination of glycemic indexes is well known to skilled artesians. For example, the glycemic index of a food may be determined by measuring the incremental area under the two-hour blood glucose response curve (AUC) following a 12-hour fast and ingestion of a food with typically 50 g available carbohydrates. The AUC of the test food is divided by the AUC of glucose and multiplied by 100 (see, for example Brouns F., et al., 2005, Nutr Res Rev 18 (1): 145-71).

Consequently, the invention relates in part to a non-therapeutic use of at least one carbohydrate with a glycemic index of less than 50 in a composition comprising at least one flavan-3-ol for increasing the bioavailability of said flavan-3-ol.

In a further aspect, the invention relates to a composition comprising at least one carbohydrate with a glycemic index of less than 50 and at least one flavan-3-ol for use in the treatment or prevention of disorders that can be treated or prevented by flavan-3-ol administration.

Figure 1:
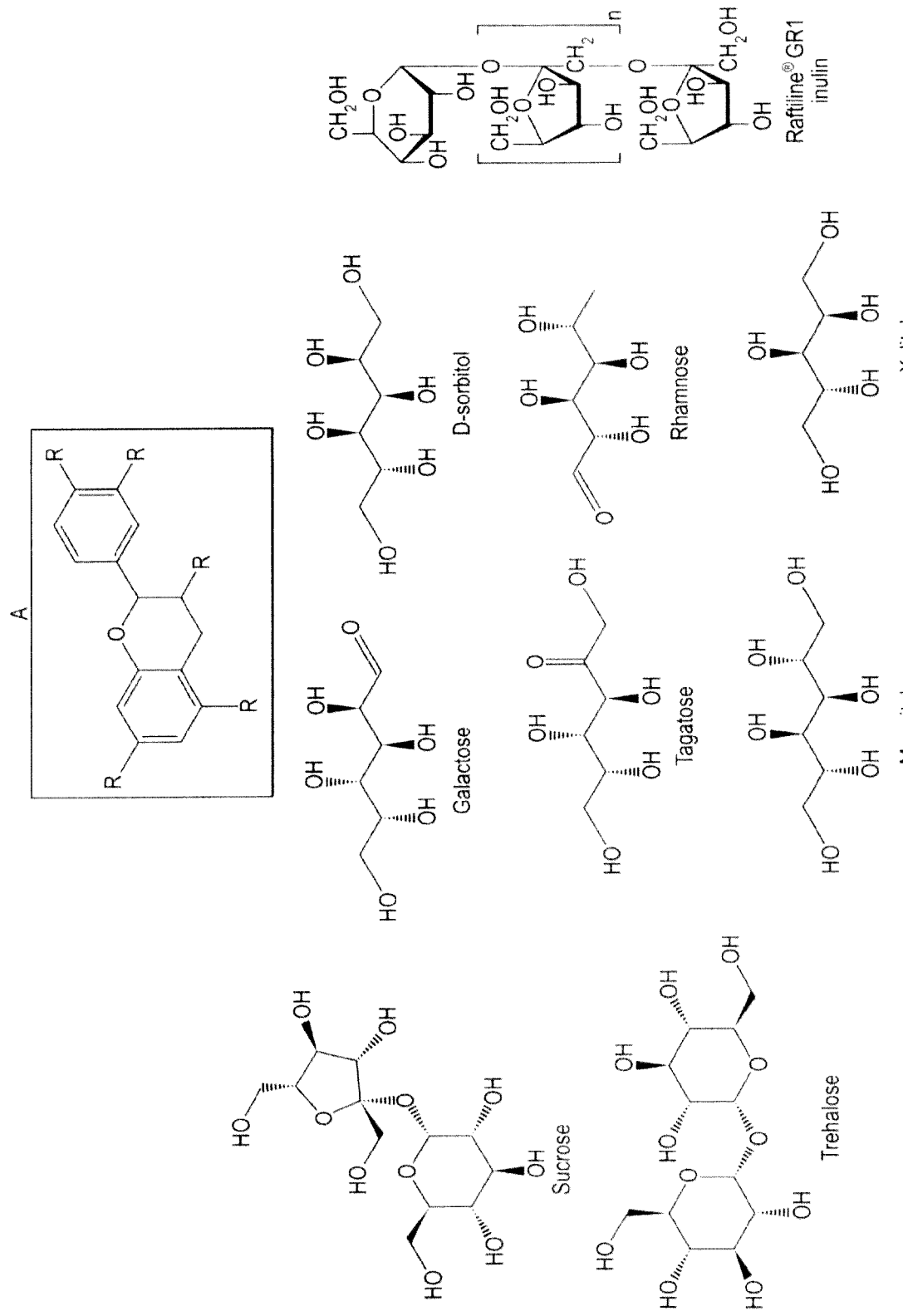
FIG. 1 shows the general formula of flavan-3-ols (A) and of carbohydrates that may form the mixture described in this invention.

Consequently the present invention relates in part to a non-therapeutic use of at least one carbohydrate with a glycemic index of less than 50 in a composition comprising at least one flavan-3-ol for increasing the bioavailability of said flavan-3-ol.

Bioavailability may be defined as the proportion of the administered substance capable of being absorbed and available for use or storage.

The present invention also relates to a composition comprising at least one flavan-3-ol for use in the treatment or prevention of disorders that can be treated or prevented by flavan-3-ol administration, wherein the composition further comprises at least one carbohydrate with a glycemic index of less than 50 for increasing the bioavailability of said flavan-3-ol.

The present invention further relates to the use of at least one flavan-3-ol for the preparation of a composition for treating or preventing disorders that can be treated or prevented by flavan-3-ol administration, wherein the composition further comprises at least one carbohydrate with a glycemic index of less than 50 for increasing the bioavailability of said flavan-3-ol.

Disorders that can be treated or prevented by flavan-3-ol administration are well known to skilled artesians. Examples of disorders that can be treated or prevented by flavan-3-ol administration may be selected from the group consisting of cardiovascular diseases, type 2 diabetes, overweight, obesity, inflammatory disorders, cognitive impairment and oxidative skin damage.

The inventors have used a Caco-2 cell model to study, how the flavan-3-ol absorption is influenced, if the flavan-3-ols are co-administered with carbohydrates.

The inventors found that the absorption of flavan-3-ols could be significantly enhanced if the flavan-3-ols were co-administered with at least one carbohydrate with a glycemic index of less than 50.

Non limiting examples of carbohydrates with a glycemic index of less than 50 include: Lactose, Fructose, Galactose, Xylitol, Glycerol, Sorbitol including D-sorbitol, Lactitol, Isomalt, Mannitol, Erythritol, Glycyrrhizin, Mogroside, Steviol glycoside.

In the experiments performed by the inventors, xylitol, galactose, D-sorbitol, or combinations thereof produced particularly good results.

Xylitol has a GI of 7. Galactose has a GI of 23. D-sorbitol has a GI of 4.

Hence, at least one carbohydrate may have a glycemic index of less than 25, for example of less than 10.

Non limiting examples of carbohydrates with a glycemic index of less than 25 include: Galactose, Xylitol, Glycerol, Sorbitol including D-sorbitol, Lactitol, Isomalt, Mannitol, Erythritol, Glycyrrhizin, Mogroside, Steviol glycoside.

The carbohydrate may be galactose. Alternatively, the carbohydrate may be D-sorbitol. The carbohydrate may also be xylitol.

This increase in absorption clearly demonstrates an improved bioavailability of flavan-3-ols if co-administered with the tested carbohydrates.

Through improving bioavailability of flavan-3-ols by co-administration with polyphenols the capacity for a beneficial change or a therapeutic effect of such a flavan-3-ol intervention is improved.

Consequently, the co-administration of flavan-3-ols with at least one carbohydrate with a glycemic index of less than 50 in accordance with the present invention allows it to increase the bioefficacy of said flavan-3-ol.

A non-therapeutic use may be a cosmetic use, for example.

The flavan-3-ols may be provided from natural sources. They may be provided as extracts from these natural sources or as the natural source itself as food ingredient, processed or unprocessed.

For example, the flavan-3-ols may originate from green tea, white tea, wild plant fruits, in particular berries, apples, cocoa beans or other fruits containing flavan-3-ols.

Green tea, the most commonly consumed beverage in the world after water, is a very good source of flavan-3-ols. Although amounts of flavan-3-ols present in green tea vary depending on factors influencing plant metabolism such as light, rain fall, temperature, nutrient availability, leaf age, and genetic make-up, they usually constitute 16-24% of the dry matter of fresh green tea leaves. As flavan-3-ols are typically stable during the manufacturing of green tea, they represent a major part of commercial green tea extracts.

The major green tea flavan-3-ols are catechins, i.e. (+)-catechin (C) and its stereoisomer and four derivatives, namely (−)-epicatechin (EC), (−)-epigallocatechin (EGC), (−)-epigallocatechin-3-gallate (EGCg), (−)-epicatechin-3-gallate (ECg).

Flavan-3-ols display several health benefits that are often associated with their antioxidant activities including scavenging of reactive oxygen and nitrogen species, free metal chelation, inhibition of transcriptional factors and inhibition of oxidative enzymes such as lipoxygenase and cycloxygenase.

In one embodiment, the flavan-3-ols are from green tea. Other sources of flavan-3-ols may alternatively be used.

Green tea or other plant sources may be used in the form of fresh, concentrated or dried materials, for example, air or freeze dried material.

For example, the flavan-3-ols used in the present invention may be selected from the group consisting of (+)-catechin (C), (−)-epicatechin (EC), gallocatechin (GC), gallocatechin gallate (GCG), (−)-epigallocatechin (EGC), (−)-epigallocatechin-3-gallate (EGCg), (−)-epicatechin-3-gallate (ECg), or combinations thereof.

In an embodiment the flavan-3-ols used in the present invention is (−)-epicatechin and/or (−)-epigallocatechin-3-gallate.

The amount of flavan-3-ols in the composition will depend on its intended application.

In therapeutic applications, active compounds are administered in an amount sufficient to at least partially cure or arrest the symptoms of a disorder and/or its complications. An amount adequate to accomplish this is defined as "a therapeutic effective dose". Amounts effective for this purpose will depend on a number of factors known to those of skill in the art such as the severity of the disorder and the weight and general state of the patient.

In prophylactic applications, active compounds according to the invention are administered to a patient susceptible to or otherwise at risk of a particular disorder in an amount that is sufficient to at least partially reduce the risk of developing a disorder. Such an amount is defined to be "a prophylactic effective dose". Again, the precise amounts depend on a number of patient specific factors such as the patient's state of health and weight.

In non-therapeutic, e.g., cosmetic applications, active compounds according to the invention are administered to a person in an amount sufficient to at least partially reduce a visible or tangible imperfection of a physical appearance of a person. Such an amount is defined to be "a cosmetic effective dose". Again, the precise amounts depend on a number of person specific factors such as the persons gender, race, complexion, age, or state of health.

In the framework of the present invention, the active compounds may be administered in a prophylactic effective dose, a therapeutic effective dose, or in a cosmetic effective dose.

The active compounds used in the present invention are flavan-3-ols.

For example, the flavan-3-ols may be present in the composition described in the present invention in an amount corresponding to 0.5-50 weight-% of the dry weight of the composition, for example 1.5-20 weight-% of the dry weight of the composition, or 2-10 weight-% of the dry weight of the composition.

In order to improve absorption and bioavailability of the flavan-3-ols optimally, an appropriate ratio of carbohydrates with a glycemic index of less than 50 and flavan-3-ols should be used.

This ideal ratio will depend on many factors, such as the nature of the food matrix, the concentration of the active compound and the details of storage and consumption, for example. Skilled artesians will be able to identify such optimal ratios.

For example, the compositions of the present invention may contain carbohydrates with a glycemic index of less than 50 and flavan-3-ols in a weight ratio in the range of 2:1 to 1:6, for example in a weight ratio in the range of 1:1 to 1:4, or in a weight ratio in the range of 1:1 to 1:3.

The composition of the present invention may be to be administered orally or it may be applied to the body surface, for example. The composition may be a foodstuff, a drink, a food supplement, a pet food product, a nutritional, or a cosmetic composition.

A food composition for human consumption may be a nutritional complete formula, a dairy product, a chilled or shelf stable beverage, a mineral or purified water, a liquid drink, a soup, a dietary supplement, a meal replacement, a nutritional bar, a confectionery, a milk or a fermented milk product, a yoghurt, a milk based powder, an enteral nutrition product, an infant formula, an infant nutritional product, a cereal product or a fermented cereal based product, an ice-cream, a chocolate, coffee, a culinary product such as mayonnaise, tomato puree or salad dressings or a pet food.

For ingestion, many embodiments of oral compositions and in particular of food supplements are possible. They may be formulated as sugar-coated tablets, pills, pastes, gums, gelatine capsules, gels, emulsions, tablets, capsules or drinkable solutions or emulsions, which can then be taken directly with water or by any other known means.

The food composition or food supplement may also include a sweetener, a stabilizer, an antioxidant, an additive, a flavouring or a colorant. The composition may also contain synthetic or natural bioactive ingredients such as amino acids, fatty acids, vitamins, minerals, carotenoids, polyphenols, etc. that can be added either by dry or by wet mixing to said composition before pasteurization and/or drying.

According to an embodiment, the composition of the invention may be used cosmetically. By "cosmetic use" is meant a non-therapeutic use which may improve the aesthetic aspect or comfort of the skin, coat and/or hair of humans or pets.

When used cosmetically, the composition of the invention may assume any form of food composition or supplement described above. Preferably, it is in the form of dietary supplements, which may be in liquid or dry form, such as solutions, sprays, tablets, capsules, gelatine capsules, lozenges, powders, gels, emulsions etc. More preferably it is in the form of a capsule. A supplement for cosmetic purpose can additionally comprise a compound active with respect to the skin.

The invention also relates to topical compositions. Such topical compositions may be formulated as lotions, shampoos, creams, sun-screens, after-sun creams, anti-ageing creams and/or ointments, for example. A composition which can be used topically may additionally comprises a fat or an oil which can be used in cosmetics, for example those mentioned in the CTFA work, Cosmetic Ingredients Handbook, Washington. It is also possible to add other cosmetically active ingredients. Such compositions may additionally comprise a structuring agent and/or an emulsifier. Other excipients, colorants, fragrances or opacifiers can also be added to the composition. It will be appreciated that cosmetic products may contain a mixture of different ingredients known to the skilled person, ensuring a fast penetration of the said substance into the skin and preventing degradation thereof during storage.

It will be understood that the concept of the present invention may likewise be applied as an adjuvant therapy assisting in presently used medications.

Those skilled in the art will understand that they can freely combine all features of the present invention disclosed herein. In particular, features described for the non-therapeutic use of the present invention may be combined with the composition for use of the present invention and vice versa. Further, features described for different embodiments of the present invention may be combined.

Although the invention has been described by way of example, it should be appreciated that variations and modifications may be made without departing from the scope of the invention as defined in the claims.

Furthermore, where known equivalents exist to specific features, such equivalents are incorporated as if specifically referred in this specification. Further advantages and features of the present invention are apparent from the figures and non-limiting examples.

EXAMPLES

In Vitro Caco 2-Cell Model

Method:

Caco-2 human epithelial colorectal adenocarcinoma cells were used to investigate the transport of (−)-epicatechin in vitro. Cells were grown in high glucose DMEM supplemented with 20% heat inactivated fetal bovine serum, non-essential amino acids and 2 mM L-glutamine, amphotericin B (1 µg/ml), penicillin (100 U/ml), and streptomycin (100 µg/ml) and maintained at 37° C. and 5% $CO_2$. The medium was replaced every 2 days and the cells were reseeded every 7 days. Then, cells were seeded in 12-well transwell inserts at a density of 20,000 cells per $cm^2$ and the medium on both sides was replaced every 2 days. After 21 days, cells were already differentiated. On the experiment day, medium was removed and replaced by HBSS supplemented with 25 mM glucose, 10 mM HEPES and 1.8 mM CaCl2. Catalase (189 U/ml) and ascorbic acid (0.5 mM) were added to prevent oxidation of the test compounds. Then, (−)-epicatechin (250 µM) alone or plus carbohydrates (5 to 100 mg/ml) were placed in the apical side of the cell monolayers and incubated for 2 h. All compounds were added to the exposure medium from stock solutions in DMSO. The concentration of DMSO at the apical side was kept at 0.05% in each experiment. (−)-Epicatechin was detected in the cell culture media using ultra-performance liquid chromatography using an Acquity UPLC HSS C18 2.1×100 mm, 1.8 µm column (Waters, Switzerland) equipped with HSS C18 VanGuard pre-column (Waters, Switzerland).

Figure 2:
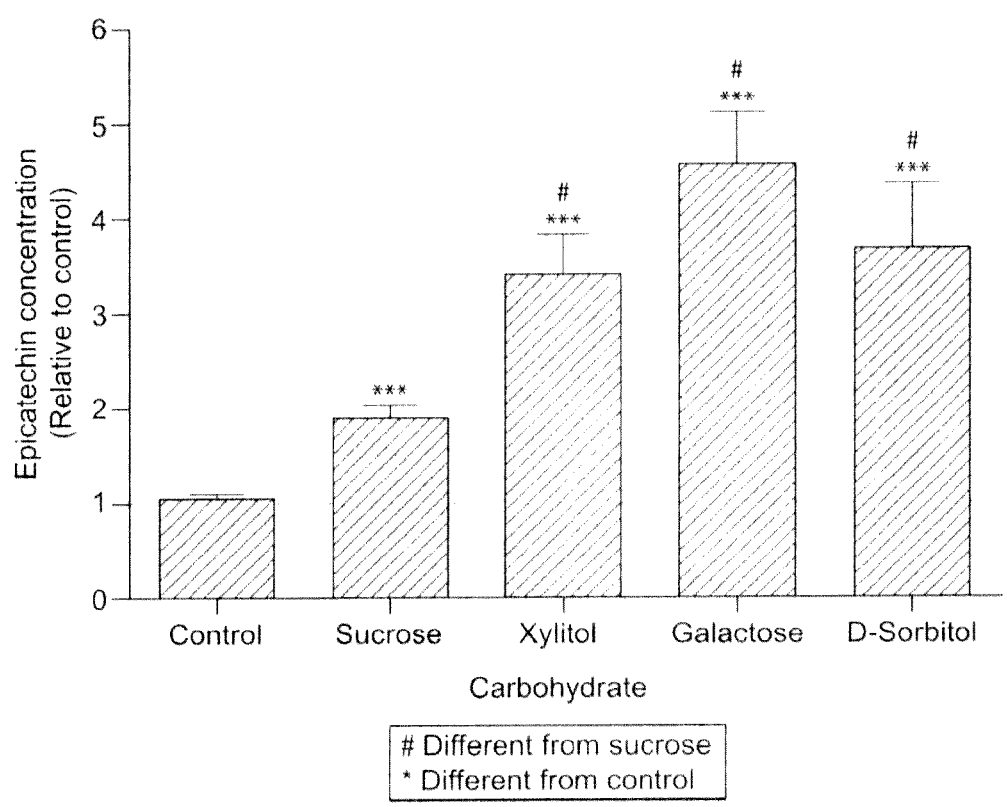
FIG. 2 shows the (−)-epicatechin concentration (relative to control) in the basal compartment after incubating 250 µM with 100 mg/ml of different carbohydrates during 2 h. Data are presented as mean±standard error.

Results:

Results obtained for all carbohydrates incubated during 2 h and tested at 100 mg/ml are shown in FIG. 2. It was observed a significant higher (−)-epicatechin transport in the presence of sucrose ($p<0.05$) when compared to control (epicatechin in medium). In comparison to sucrose, xylitol, galactose and sorbitol had a significant higher concentration of (−)-epicatechin in the basal compartment.

The results obtained from this in vitro model showed that, when in combination with some selected carbohydrates (particularly low glycemic index such as xylitol, galactose and sorbitol), there was a significant increase in the concentration of (−)-epicatechin in the basal compartment, indicating that this compound was better absorbed.

The invention claimed is:

1. A non-therapeutic method of increasing the bioavailability of at least one flavan-3-ol to reduce a visible or tangible imperfection of skin of an individual having the visible or tangible imperfection, the method comprising administering a composition to the individual having the visible or tangible imperfection, the composition comprising the at least one flavan-3-ol and a carbohydrate consisting of galactose, wherein the composition comprises the carbohydrate and the at least one flavan-3-ol in a weight ratio of 1:1 to 1:3, wherein the at least one flavan-3-ol is selected from the group consisting of (+)-catechin (C), (−)-epicatechin (EC), gallocatechin (GC), gallocatechin gallate (GCG), (−)-epigallocatechin (EGC), (−)-epigallocatechin-3-gallate (EGCg), (−)-epicatechin-3-gallate (ECg), and mixtures thereof.

2. The non-therapeutic method of claim 1 wherein the at least one flavan-3-ol originates from at least one source selected from the group consisting of green tea, wild plant fruits, apples, cocoa beans and other fruits containing flavan-3-ols.

3. The non-therapeutic method of claim 1 wherein the composition is selected from the group consisting of a foodstuff, a drink, a food supplement, a pet food product, a nutritional, and cosmetic composition.

4. The non-therapeutic method of claim 1 wherein the composition further comprises at least one component selected from the group consisting of a stabilizer, a flavoring ingredient and a colorant.

5. The non-therapeutic method of claim 1 wherein the administration step is consuming the composition orally.

6. The non-therapeutic method of claim 1 wherein the bioavailability of the at least one flavan-3-ol is increased by increasing absorption and/or bioefficacy of the at least one flavan-3-ol.

7. The non-therapeutic method of claim 1 wherein the composition is administered to the individual in a cosmetically effective dose.

8. A method for treatment of at least one disorder selected from the group consisting of cardiovascular diseases, inflammatory disorders, cognitive impairment and oxidative skin damage, the method comprising administering to an individual having the at least one disorder a composition comprising (i) at least one carbohydrate comprising galactose and D-Sorbitol, and (ii) at least one flavan-3-ol, wherein the composition comprises the at least one carbohydrate and the at least one flavan-3-ol in a weight ratio of 1:1 to 1:3, wherein the at least one flavan-3-ol is selected from the group consisting of (+)-catechin (C), (−)-epicatechin (EC), gallocatechin (GC), gallocatechin gallate (GCG), (−)-epigallocatechin (EGC), (−)-epigallocatechin-3-gallate (EGCg), (−)-epicatechin-3-gallate (ECg), and combinations thereof.

9. The method of claim 8, wherein the disorder is a cardiovascular disease.

10. The method of claim 8, wherein the disorder is an inflammatory disorder.

11. The method of claim 8, wherein the disorder is cognitive impairment.

12. The method of claim 8, wherein the disorder is oxidative skin damage.

13. The method of claim 8 wherein the administering of the composition comprises consuming the composition orally.

14. The method of claim 8 wherein the composition is administered to the individual in a therapeutically effective dose.

15. A non-therapeutic method of increasing the bioavailability of at least one flavan-3-ol to reduce a visible or tangible imperfection of skin of an individual having the visible or tangible imperfection, the method comprising administering a composition to the individual having the visible or tangible imperfection, the composition comprising galactose and the at least one flavan-3-ol, wherein the composition comprises the galactose and the at least one flavan-3-ol in a weight ratio of 1:1 to 1:3, wherein the at least one flavan-3-ol is selected from the group consisting of (+)-catechin (C), (−)-epicatechin (EC), gallocatechin (GC), gallocatechin gallate (GCG), (−)-epigallocatechin (EGC), (−)-epigallocatechin-3-gallate (EGCg), (−)-epicatechin-3-gallate (ECg), and combinations thereof.

16. The non-therapeutic method of claim 15 wherein the administering of the composition comprises consuming the composition orally.

17. The method of claim 15 wherein the composition is administered to the individual having the visible or tangible imperfection in a therapeutically effective dose.

* * * * *